(12) United States Patent
Ishikawa

(10) Patent No.: US 11,419,500 B2
(45) Date of Patent: Aug. 23, 2022

(54) IMAGING APPARATUS

(71) Applicant: Shimadzu Corporation, Kyoto (JP)

(72) Inventor: Akihiro Ishikawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 1115 days.

(21) Appl. No.: 15/909,129

(22) Filed: Mar. 1, 2018

(65) Prior Publication Data

US 2019/0269332 A1 Sep. 5, 2019

(51) Int. Cl.
*A61B 5/00* (2006.01)
*G16H 30/40* (2018.01)
*A61K 49/00* (2006.01)

(52) U.S. Cl.
CPC .......... *A61B 5/0071* (2013.01); *A61B 5/0077* (2013.01); *A61B 5/7425* (2013.01); *A61K 49/0017* (2013.01); *G16H 30/40* (2018.01); *A61B 5/0013* (2013.01)

(58) Field of Classification Search
CPC ... A61B 5/0013; A61B 5/0071; A61B 5/0077; A61B 5/7425; A61K 49/0017; A61K 49/0021; A61K 49/0034; G16H 30/20; G16H 30/40; G16H 40/63
See application file for complete search history.

(56) References Cited

U.S. PATENT DOCUMENTS

2002/0102028 A1 8/2002 Keller et al.
2009/0285760 A1 11/2009 Ishikawa et al.
2012/0134410 A1 5/2012 Kawasaki et al.
2013/0044126 A1 2/2013 Yamada
2015/0104396 A1 4/2015 Ishikawa et al.

FOREIGN PATENT DOCUMENTS

| JP | H10-248805 A | 9/1998 |
|---|---|---|
| JP | 2002-352220 A | 12/2002 |
| JP | 2005-204906 A | 8/2005 |
| JP | 2010-288186 A | 12/2010 |
| JP | 2013-039223 A | 2/2013 |
| WO | 2009/139466 A1 | 11/2009 |

OTHER PUBLICATIONS

Office Action dated Jul. 17, 2018 in corresponding Japanese Application No. 2015-165450; 9 pages.

*Primary Examiner* — Mark D Remaly
(74) *Attorney, Agent, or Firm* — Maier & Maier, PLLC

(57) ABSTRACT

The control unit includes, as a mechanical configuration, an image processing unit and a recording control unit. The image processing unit includes a combining unit that combines the fluorescence image acquired by the illuminating/photographing unit and the visible light image, a condition designation unit that designates an analysis condition and the like of an image analysis by an analyzing unit to be described later, and an analyzing unit that performs an analysis under the analysis condition designated by the condition designation unit. The storage unit includes an image storage unit including a reproduction moving image storage unit that stores a combined moving image obtained by combining the fluorescence image and the visible light image by the combining unit in the image processing unit as an irreversibly-compressed moving image file and an analysis moving image storage unit that stores a fluorescence moving image and a visible light moving image.

4 Claims, 4 Drawing Sheets

IMAGING APPARATUS

FIELD

The present invention relates to an imaging apparatus that irradiates fluorescence substance that infiltrated into a body of a subject with excitation light and photographs fluorescence that is emitted from the fluorescence substance.

BACKGROUND

A technique called near-infrared fluorescence imaging is used for angiography in surgical operation. In this near-infrared fluorescence imaging, indocyanine green (ICG) which is a fluorescence dye is injected into an affected part. When the indocyanine green is irradiated with near-infrared light having a wavelength of about 810 nm (nanometer) as excitation light, indocyanine green emits near-infrared fluorescence having a wavelength of approximately 845 nm. The fluorescence is photographed by an image pickup element capable of detecting the near-infrared light, and the image is displayed on a display unit of a liquid crystal display panel or the like. According to the near-infrared fluorescence imaging, blood vessels, lymphatic vessels, and the like existing at a depth of about 20 mm from a body surface may be observed.

Further, in recent years, a method of fluorescently labeling a tumor and using it for surgical navigation has attracted attention. As a fluorescence labeling agent for fluorescently labeling the tumor, 5-aminolevulinic acid (5-ALA) is used. When the 5-aminolevulinic acid (hereinafter, referred to as "5-ALA" when abbreviated) is administered to the subject, the 5-ALA is metabolized to PpIX (protoporphyrinlX/protoporphyrin nine) which is a fluorescence substance. The PpIX is accumulated in cancer cells specifically. When the PpIX which is a metabolite of 5-ALA is irradiated with visible light having a wavelength of about 410 nm, red visible light having a wavelength of about 630 nm is emitted as fluorescence from the PpIX. By observing the fluorescence from this PpIX, cancer cells can be confirmed.

International Publication No. 2009/139466 discloses a data collection method in which an intensity distribution image of near-infrared fluorescence obtained by irradiating a test organ of a living body to which the indocyanine green has been administered with excitation light of the indocyanine green and a cancer lesion distribution image obtained by applying X-ray, nuclear magnetic resonance or ultrasonic wave to the test organ before the indocyanine green is administrated are compared, and data of an area which is detected in the intensity distribution image of the near-infrared fluorescence but is not detected in the cancer lesion distribution image is collected as a secondary cancer lesion area data.

SUMMARY

Such an imaging apparatus for photographing the fluorescence from the fluorescence substance that infiltrated into the body is configured that a single camera photographs visible light and near-infrared light at the same time and a photographed image recorded by a video recorder is reproduced as a moving image. As such, in the related-art imaging apparatus, the image photographed at a predetermined frame rate is recorded/reproduced as a moving image, so that running of a blood vessel and a lymphatic vessel may be observed after the ICG is administrated or a cancer lesion area may be confirmed under a bright external illumination environment.

Meanwhile, the data constituting the moving image is encoded by a moving-image compression technology (Codec) of a high compression rate in order to perform a light handling of data, such as reducing a data transmission load and facilitating a data reproduction, and is stored in a file format that can be handled by a moving image reproduction device or an application. Then, a moving image file storing the data irreversibly compressed by Codec is stored in the storage device or the like. The compressed moving image file is decompressed by Codec used when compressing data at the time of reproducing the moving image. An image of each frame of the moving image once compressed in the irreversible compression format is degraded in image quality as compared with the image of each uncompressed frame before the compression. For this reason, it was difficult to utilize an image data of the irreversibly-compressed moving image file that is generated for the purpose of reproduction for quantitative evaluation and the like utilizing various image processing techniques.

The present invention was made to solve the aforementioned problem, and intends to provide an imaging apparatus capable of collecting image data that can be used for image analysis.

The present invention according to claim 1 includes: an excitation light source that irradiates a fluorescence substance infiltrated into a body of a subject with excitation light; a visible light source that irradiates the subject with white light; a photographing unit that detects and photographs a fluorescence excited by the excitation light and generated from the fluorescence substance and a reflected light of the white light; an image processing unit including a combining unit that creates a combined image obtained by combining a fluorescence image and a visible light image acquired by simultaneously photographing the fluorescence and the reflected light at a predetermined frame rate with the use of the photographing unit; and an image storage unit that stores the fluorescence image, the visible light image and the combined image respectively. The image storage unit includes a first moving image storage unit that stores each of the fluorescence image, the visible light image and the combined image as an irreversibly-compressed moving image file of high compression rate, and a second moving image storage unit that stores each of the fluorescence image and the visible light image as a reversibly-compressed moving image file or an uncompressed moving image file.

According to the invention, the image processing unit includes a condition designation unit that designates a frame to be subjected to an image analysis when the irreversibly-compressed moving image file is reproduced and an analysis condition and an analyzing unit that extracts a frame corresponding to the frame of the irreversibly compressed moving image file, which was designated in the condition designation unit, from the reversibly-compressed moving image file or the uncompressed moving image file and performs an image analysis, wherein an analysis result in the analyzing unit is displayed on a display unit.

The invention includes a recording control unit that performs start and stop of recording at the time of generating the reversibly-compressed moving image file or the uncompressed moving image file, in synchronization with a start and a stop of recording at the time of generating the irreversibly-compressed moving image file.

The invention includes a recording control unit that designates start and stop of recording at the time of generating the reversibly-compressed moving image file or the uncompressed moving image file, apart from start and stop of recording at the time of generating the irreversibly-compressed moving image file.

According to the invention, the image storage unit includes a first moving image storage unit that stores the image acquired by the photographing unit as the irreversibly-compressed moving image file with the high compression ratio, and a second moving image storage unit that stores the image as the reversibly-compressed moving image file or the uncompressed moving image file. Therefore, it is possible to perform a moving image reproduction similar to that in the related art, and it is possible to collect moving images of image quality that can be used for various image analyses.

According to the invention, the image processing unit includes the condition designation unit that designates the frame to be subjected to the image analysis when the irreversibly-compressed moving image file is reproduced and the analysis condition, and an analyzing unit that extracts the frame corresponding to the frame of the irreversibly compressed moving image file, which was designated in the condition designation unit, from a decompressed moving image file which is decompressed from the reversibly-compressed moving image file or the uncompressed moving image file and performs the image analysis. Therefore, the operator can easily specify an image analysis range in the uncompressed or reversibly-compressed moving image file while watching the reproduced image of the irreversibly-compressed moving image file displayed on the display unit, and it becomes possible to acquire analysis results using image analysis techniques such as spatial, temporal, and quantitative analysis, which could not be obtained by an image quality of the image data stored in the irreversibly-compressed moving image file in the related art.

According to the invention, since the recording of all the moving images to be collected starts and stops in synchronization in accordance with the operation of the recording control unit, it becomes possible to easily acquire the reversibly-compressed moving image file or uncompressed moving image file storing image data of image quality that can be used for various image analysis at the same time with the acquisition of the irreversibly-compressed moving image file that is a moving image to be displayed on the display unit.

According to the invention, the recording control unit operates to control the start and the stop of recording of the moving image that is stored as the reversibly-compressed moving image file or the uncompressed moving image file, apart from the acquisition of the irreversibly-compressed moving image file to be displayed on the display unit. Therefore, it is possible to reduce a size by setting the reversibly-compressed moving image file or the uncompressed moving image file whose file size is larger than a file size of the irreversibly-compressed moving image file as a moving image file only in a time range necessary for analysis, and it is possible to reduce a load on storing, transferring and the like of the moving image file.

DETAILED DESCRIPTION OF THE DRAWINGS

Figure 1:
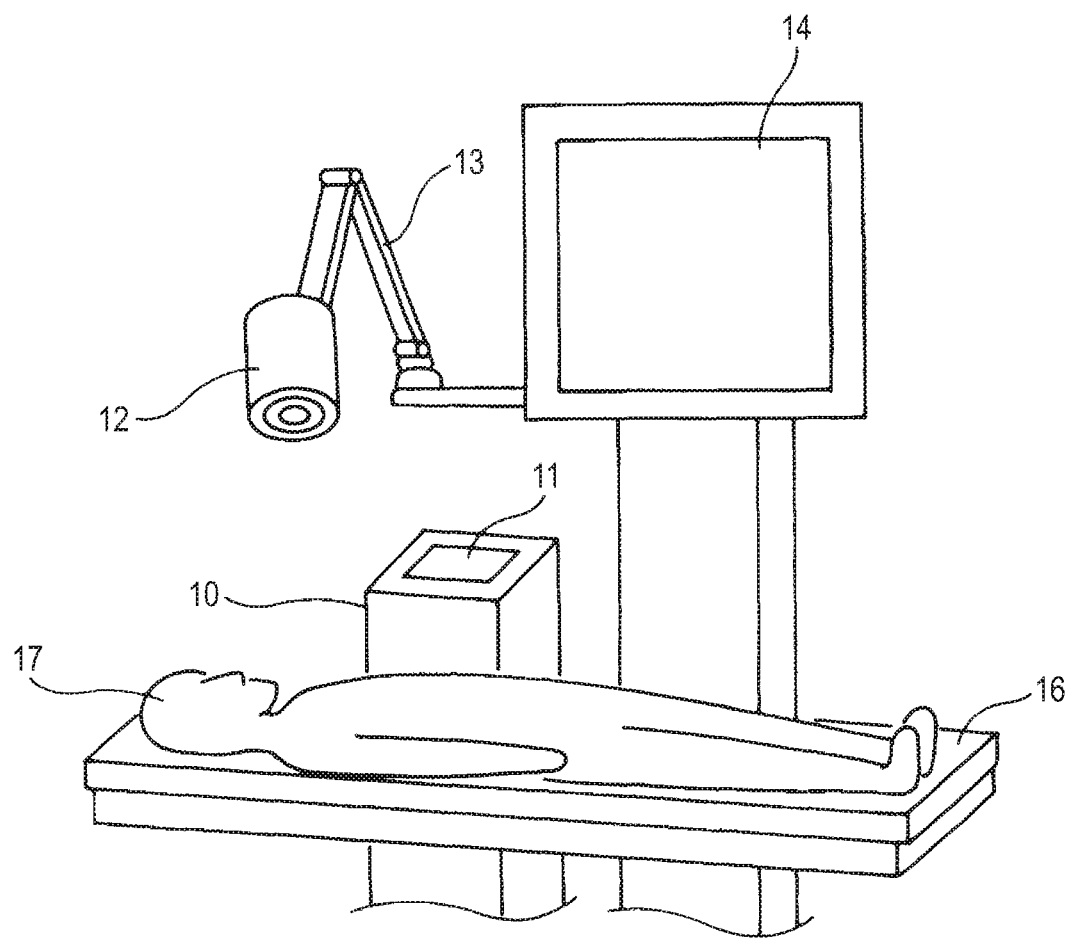
FIG. 1 is a schematic diagram of an imaging apparatus according to the present invention.

Hereinafter, embodiments of the present invention will be described with reference to the drawings. FIG. 1 is a schematic diagram of an imaging apparatus according to the present invention.

The imaging apparatus includes a main body 10 including an input unit 11 such as a touch panel and having a control unit 30, a storage unit 40 and the like to be described later incorporated therein, an illuminating/photographing unit 12 movably supported by an arm 13, a display unit 14 including a liquid crystal display panel and the like, and a treatment table 16 on which a patient 17 is placed. The illuminating/photographing unit 12 is not limited to the one supported by the arm 13, but may be carried by an operator in hand or fixed to an existing facility.

Figure 2:
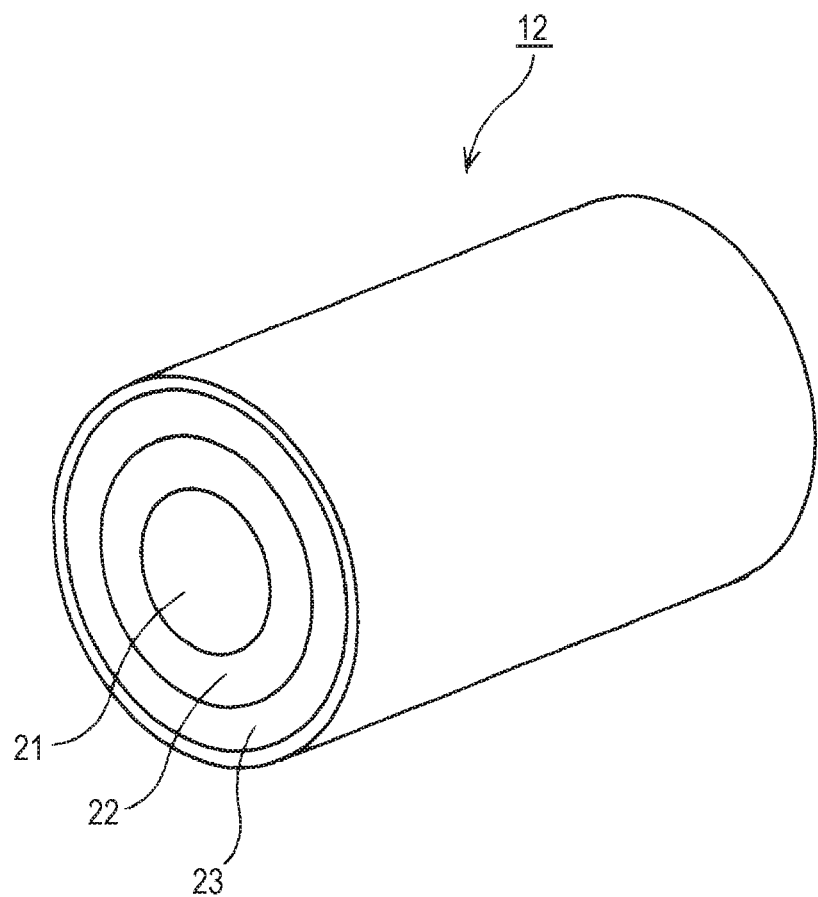
FIG. 2 is a schematic diagram of an illuminating/photographing unit 12.

FIG. 2 is a perspective view of the illuminating/photographing unit 12.

The illuminating/photographing unit 12 includes a camera 21 capable of detecting near-infrared light and visible light, an infrared light source 22 disposed on an outer periphery of the camera 21, and a visible light source 23 disposed on an outer periphery of the infrared light source 22. The infrared light source 22 is an excitation light source that excites a fluorescence substance that has infiltrated into a body of the patient 17. Further, the visible light source 23 irradiates the patient 17 with white light.

In the present embodiment, the illuminating/photographing unit 12 integrating the infrared light source 22 and the visible light source 23 and the camera 21 is used, but the infrared light source 22, the visible light source 23, and the camera 21 may be individually disposed. When only the fluorescence image is displayed on the display unit 14, the visible light source 23 may not be provided.

Figure 3:
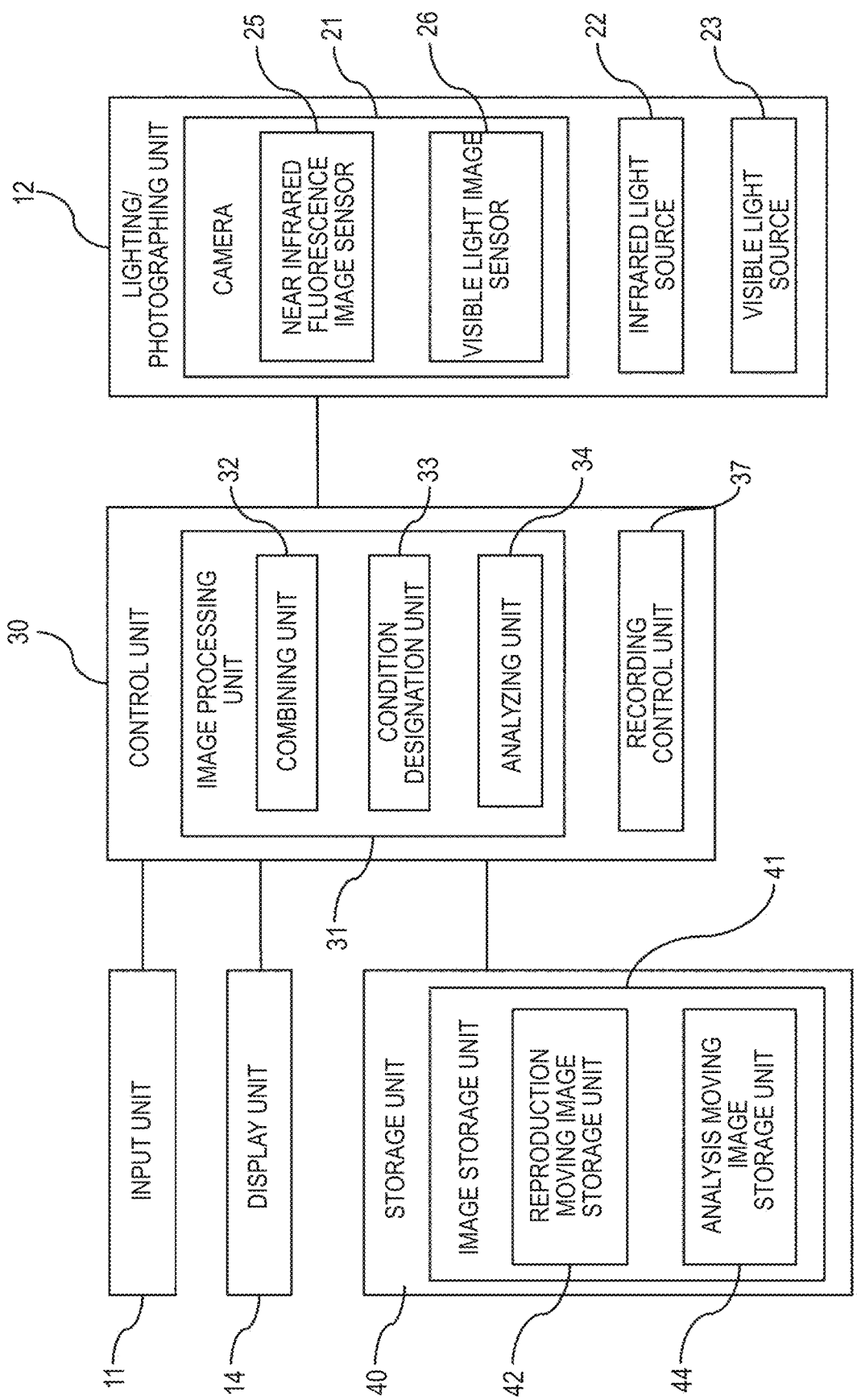
FIG. 3 is a block diagram illustrating a main control system of an imaging apparatus according to the present invention.

FIG. 3 is a block diagram illustrating a main control system of the imaging apparatus according to the present invention.

The imaging apparatus includes a CPU for executing a logical operation, a ROM in which programs necessary for generating and reproducing the moving image including a plurality of Codec and programs necessary for controlling the apparatus are stored, a RAM in which data is temporarily stored during control, and the like, and includes a control unit 30 for controlling the entire apparatus. The control unit 30 is connected to the input unit 11 and the display unit 14 described above.

Further, the control unit 30 is connected to the illuminating/photographing unit 12 including the camera 21, the infrared light source 22, and the visible light source 23. The camera 21 includes a near-infrared fluorescence image sensor 25 as an image sensor for detecting near-infrared fluorescence and a visible light image sensor 26 as an image sensor for detecting reflected light (visible light) of the white light. The fluorescence and the visible light incident on the camera 21 are separated by a spectroscopic mechanism inside the camera 21 and detected by each image sensor. Then, a fluorescence image and a visible light image detected by each image sensor are sent to the control unit 30. Since the camera 21 includes the near-infrared fluorescence image sensor 25 and the visible light image sensor 26, the imaging apparatus may acquire the fluorescence image and the visible light image synchronously in the same field of vision.

The control unit 30 includes, as a mechanical configuration, an image processing unit 31 and a recording control unit 37. The image processing unit 31 includes a combining unit 32 that combines the fluorescence image acquired by the illuminating/photographing unit 12 and the visible light image, a condition designation unit 33 that designates an analysis condition and the like of an image analysis by an analyzing unit 34 to be described later, and an analyzing unit 34 that performs an analysis under the analysis condition designated by the condition designation unit 33. The recording control unit 37 controls start and stop of a moving image recording of the fluorescence image acquired by the illuminating/photographing unit 12, the visible light image and the combined image combined by the combining unit 32.

Further, the control unit 30 is connected to a storage unit 40 that stores the image and the like photographed by the camera 21. The storage unit 40 includes an image storage unit 41 including a reproduction moving image storage unit 42 that stores a combined moving image data obtained by combining the fluorescence image and the visible light image by the combining unit 32 in the image processing unit 31 as an irreversibly-compressed moving image file and an analysis moving image storage unit 44 that stores a fluorescence moving image data and a visible light moving image data as an uncompressed or reversibly-compressed moving image file. The reproduction moving image storage unit 42 corresponds to a first moving image storage unit of the present invention and the analysis moving image storage unit 44 corresponds to the second moving image storage unit of the present invention. Although the first moving image storage unit and the second moving image storage unit are described as a functional configuration of the image storage unit 41 in this embodiment, the first moving image storage unit and the second moving image storage unit may be configured as a physically separated storage device.

Hereinafter, an operation in a surgical operation using the imaging apparatus according to the present invention will be described. The case of performing a fluorescence angiography on the patient 17 during an operation will be described as an example.

In the case of performing a fluorescence angiography using the imaging apparatus according to the present invention during a surgical operation, indocyanine green is injected by injection into the patient 17 lying on the treatment table 16. Then, the subject including an affected part is irradiated with infrared light emitted from the infrared light source 22 and white light emitted from the visible light source 23. As the infrared light, the near-infrared light of 750 to 850 nm used as excitation light that causes the indocyanine green to emit fluorescence is adopted. Thus, the indocyanine green generates fluorescence of a near-infrared area having a peak at 845 nm.

Then, the vicinity of the affected part of the patient 17 is photographed by the camera 21. The photographing is started in response to an operator's input from the input unit 11. The camera 21 is capable of detecting an infrared light and a visible light. The fluorescence image and the visible light image photographed by the camera 21 are sent to the image processing unit 31 illustrated in FIG. 3. The image processing unit 31 converts the fluorescence image and the visible image into an image data that can be displayed on the display unit 14. That is, the fluorescence image is converted into an 8-bit image data, and the visible light image is converted into a 24-bit image data formed of three colors of RGB.

The image photographed by the camera 21 is collected at a predetermined frame rate by the operation of the recording control unit 37. Then, in the image processing unit 31, a fluorescence moving image and a visible light moving image which are continuous image data are generated, and encoded by a Codec of a reversible compression format as necessary. The fluorescence moving image and the visible light moving image are stored in a file format and are stored as an uncompressed moving image file or a reversibly-compressed moving image file in the analysis moving image storage unit 44 of the image storage unit 41. In addition, the fluorescence image and the visible light image of each frame of the fluorescence moving image and the visible light moving image are combined by the combining unit 32 and become a combined moving image. The combined moving image is encoded in the irreversible compression format and then stored in the file format, and is stored in the reproduction moving image storage unit 42 of the image storage unit 41 as an irreversibly-compressed moving image file. The combined moving image stored as an irreversibly-compressed moving image file in the reproduction moving image storage unit 42 is displayed on the display unit 14 for observation immediately after the stored or after a certain period of time.

In this imaging apparatus, start and end of generation of the combined moving image and start and end of generation of the uncompressed or irreversibly-compressed fluorescence moving image and the visible light moving image are synchronized by the operation of the recording control unit 37. That is, since start and stop of recording of the reproduction moving image and start and stop of recording of the analysis moving image are synchronized with each other in this imaging apparatus, it is possible to acquire at least three moving image files of the combined moving image displayed on the display unit 14, the fluorescence moving image and the visible light moving image that have the same time axis as the combined moving image and hold image data that is not deteriorated in image quality at the time of recording and subsequent reproduction.

Figure 4:
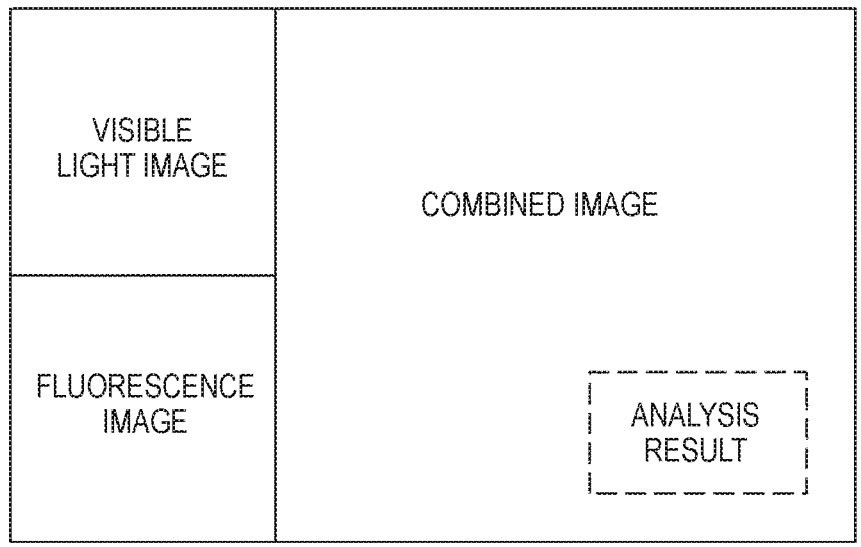
FIG. 4 is a schematic diagram illustrating an example of a display mode of an image on a display unit 14.
Figure 5:
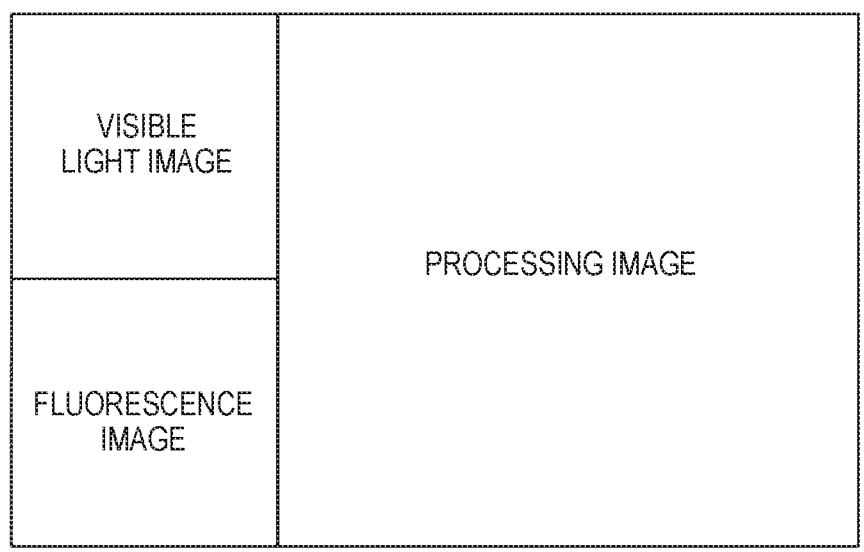
FIG. 5 is a schematic diagram illustrating an example of a display mode of an image on the display unit 14.

FIGS. 4 and 5 are schematic diagrams illustrating an example of a display mode of an image on the display unit 14.

As illustrated in FIGS. 4 and 5, display areas of a fluorescence image, a visible light image, a combined image or a processed image described later are provided on the display unit 14, and respective images are displayed. In the display areas of the fluorescence image and the visible light image, for example, a still image extracted at a predetermined frame interval from an uncompressed moving image file stored in the analysis moving image storage unit 44 is displayed. The fluorescence moving image or the visible light moving image may be stored as the irreversibly-compressed moving image file in the reproduction moving image storage unit 42. In this case, the fluorescence moving image or the visible light moving image may also be reproduced in the display areas of the fluorescence image and the visible light image. Further, the combined moving image stored as the irreversibly-compressed moving image file in the reproduction moving image storage unit 42 is played in the display area of the combined image illustrated in FIG. 4.

In response to an input from the input unit 11 by the operator, the condition designation unit 33 executes designation of a frame for an image analysis and designation of an analysis condition. For example, the designation of the frame for the image analysis may be performed by the operator touching a button associated with the analysis menu, such as a button for designating a range to be subjected to the image analysis in the moving image provided on a touch panel of the input unit 11, while watching a moving image being reproduced in the display area of the combined image of the display unit 14 illustrated in FIG. 4. At this time, a frame for performing the image analysis in the moving image file stored in the analysis moving image storage unit 44 is also determined according to a temporal correspondence relationship of each frame of a reproduction moving image file and the moving image file stored in the analysis moving image storage unit 44. That is, while conducting an observation with the reproduction moving image similar to that in the related art, the operator can easily select a desired frame of the moving image file stored in the analysis moving image storage unit 44 as an object of the image analysis. The designation of the frame to be subjected to such an image analysis can also be performed by inputting numerical values of a frame number, selection of a recording time range of the moving image and the like.

In addition, not only the input by the touch panel of the input unit 11 described above but also other input means can be used to designate the frame to be subjected to the image analysis in the condition designation unit 33. For example, a touch panel may be provided on the display unit 14, and a frame to be subjected to the image analysis may be designated by touching a combined image being reproduced in the display area of the combined image of the display unit 14 illustrated in FIG. 4. Further, a mouse may be separately added as an input device, and when the combined moving image is being reproduced in the display area of the combined image of the display unit 14, the operator may click the mouse to designate the frame for the image analysis.

The designation of the analysis condition in the condition designation unit 33 is executed, for example, by the operator touching a condition selection button provided on the touch panel of the input unit 11. A spatial analysis such as a running direction of the blood vessel and the lymphatic vessel, a temporal analysis and a quantitative analysis of blood flow in the blood vessel, a comparative analysis of the blood flow before and after treatment, etc. are prepared as an analysis menu in advance, and the analysis condition can be designated by selecting the analysis condition from the analysis menu.

The analyzing unit 34 extracts a frame corresponding to a combined moving image frame in the combined moving image to be subjected to the analysis designated by the condition designation unit 33, from the uncompressed fluorescence moving image file and/or the visible light moving image file stored in the analysis moving image storage unit 44 or the data obtained by decompressing the reversibly-compressed fluorescence moving image file and/or the visible light moving image file respectively. Thereafter, for an image of each frame in which the deterioration of image quality does not occur, the analysis is executed according to the analysis condition designated by the condition designation unit 33.

The analysis result by the analyzing unit 34 is displayed on the display unit 14. For example, in the case of designating a blood vessel whose blood flow is to be monitored or an affected area of the blood vessel in the moving image as an area of interest and performing image analysis of a frame extracted from the fluorescence moving image, for example, a display area of the analysis result is provided while being superimposed on the area where the combined moving image is being reproduced, and the analysis result is displayed on the display area using a table such as a graph showing a numerical value or time variation, as illustrated in FIG. 4.

In addition, when comparing states of the blood flow before and after the operation, for example, a processed image obtained by superimposing a fluorescence image of a certain frame before the operation on a combined moving image after the operation may be displayed, as illustrated in FIG. 5.

Next, a modified example of the imaging apparatus according to the present invention will be described.

In the embodiment described above, the recording control unit 37 performs the recording control to record and store all of the moving images to be recorded (the fluorescence moving image, the visible light moving image and the combined moving image) in a synchronized manner, regardless of a format in which they are stored among a uncompressed format, a reversibly-compressed format, and a irreversibly-compressed format. Meanwhile, in the recording control unit 37 of this modified example, start and stop of recording are separately controlled between the irreversibly-compressed moving image (combined moving image) and the uncompressed or reversibly-compressed moving image (fluorescence moving image and the visible light moving image). Such a variation of the control is realized by providing a touch panel type input unit 11 with input buttons for starting and stopping recording for each type of the moving image to be collected and storing a program for executing an operation in response to input from these input buttons in the ROM of the control unit 30.

In the case of operating the recording control unit 37 as in this modified example, time information described in each moving image file is read using a clock function provided in the control unit 30, and time of each frame of irreversibly-compressed combined moving image file is combined with time of each frame of an uncompressed or reversibly-compressed fluorescence moving image file. As a result, frames at the same time are extracted from the uncompressed or reversibly-compressed fluorescence moving image file and/or the uncompressed or reversibly-compressed visible light moving image file. By associating the time axes between the moving image files having different recording times in this way, it is possible to ensure a concurrency between each frame in the combined moving image to be reproduced on the display unit 14 and each frame of the fluorescence moving image and the visible light moving image used for image analysis in the analyzing unit 34.

In general, the reversibly-compressed moving image file has a compression rate lower than that of the irreversibly-compressed moving image file and has a data capacity larger than that of irreversibly-compressed moving image file, and the uncompressed moving image file has a large data capacity. In the above-described modified example, since data unnecessary for the image analysis is not stored, it is possible to avoid a situation where data storage capacity of the storage unit 40 is insufficient, and it is possible to reduce the data transfer load when each frame image of the moving image is used later.

Further, in the aforementioned embodiment, a case where indocyanine green is used for angiography of the patient 17 has been described. However, the present invention may also be applied to the case of using other fluorescence labeling agent such as 5-ALA which is metabolized to protoporphyrin IX (PpIX) which is a fluorescence substance in a cancer cell.

The invention claimed is:

1. An imaging apparatus comprising:
a first light source that irradiates a fluorescence substance infiltrated into a body of a subject with excitation light;
a second light source that irradiates the subject with white light;
a camera that detects and simultaneously photographs a fluorescence excited by the excitation light and generated from the fluorescence substance and a reflected light of the white light, to acquire a fluorescence image and a visible light image,
wherein the imaging apparatus is configured to:
generate either an uncompressed moving image file, which is a fluorescence moving image and a visible light moving image, by collecting at a predetermined frame rate the fluorescence image and the visible light image or a reversibly-compressed moving image file by encoding the fluorescence moving image and the visible light moving image in a reversible compression format;
create a combined moving image by combining the fluorescence image and the visible light image of each frame of the fluorescence moving image and the visible light moving image;
generate an irreversibly-compressed moving image file by encoding the combined moving image in an irreversible compression format; and
store the irreversibly-compressed moving image file, and either the uncompressed moving image file or the reversibly-compressed moving image file.

2. The imaging apparatus according to claim 1, further configured to:
designate an analysis condition and a frame to be subjected to an image analysis when the irreversibly-compressed moving image file is reproduced; extract a frame corresponding to the designated frame of the irreversibly compressed moving image file from the reversibly-compressed moving image file or the uncompressed moving image file and performs the image analysis; and
display an analysis result on a display unit.

3. The imaging apparatus according to claim 1, further configured to perform a start and a stop of recording at the time of generating the reversibly-compressed moving image file or the uncompressed moving image file, in synchronization with a start and a stop of recording at the time of generating the irreversibly-compressed moving image file.

4. The imaging apparatus according to claim 1, further configured to designate a start and a stop of recording at the time of generating the reversibly-compressed moving image file or the uncompressed moving image file, apart from a start and a stop of recording at the time of generating the irreversibly-compressed moving image file.

* * * * *